US00PP12587P2

(12) United States Plant Patent
Gross

(10) Patent No.: US PP12,587 P2
(45) Date of Patent: Apr. 30, 2002

(54) POINSETTIA PLANT NAMED 'EDA PAN 1'

(75) Inventor: Eduard Gross, Blanzac (FR)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 09/563,937

(22) Filed: May 4, 2000

(51) Int. Cl.[7] ..... A01H 5/00
(52) U.S. Cl. ..... Plt./307

(58) Field of Search ..... Plt./307

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Poinsettia plant named 'Eda Pan 1', characterized by its bright red bract; green, lighter green and light yellow variegated leaves; compact, uniform and upright plant habit; and excellent post-production longevity.

1 Drawing Sheet

BACKGROUND OF THE INVENTION

The present Invention relates to a new and distinct cultivar of Poinsettia plant, botanically known as *Euphorbia pulcherrima* Willd., and hereinafter referred to by the name 'Eda Pan 1'.

The new Poinsettia is a naturally-occurring whole plant mutation of the *Euphorbia pulcherrima* Willd. cultivar Supjisil, not patented. The new Poinsettia was discovered and selected by the Inventor in a controlled environment in Blanzac, France. Compared to plants of the parent cultivar, plants of the new Poinsettia are shorter, have smaller flower bracts and brighter red flower bract color.

Asexual reproduction of the new Poinsettia by terminal cuttings taken at Encinitas, Calif., has shown that the unique features of this new Poinsettia are stable and reproduced true to type in successive generations of asexual reproduction.

BRIEF SUMMARY OF THE INVENTION

The following traits have been repeatedly observed and are determined to be the unique characteristics of 'Eda Pan 1'. These characteristics in combination distinguish 'Eda Pan 1' as a new and distinct cultivar:

1. Bright red bracts.
2. Green, lighter green and light yellow variegated leaves.
3. Compact, uniform and upright plant habit.
4. Excellent post-production longevity.

Plants of the new Poinsettia are similar to plants of the Poinsettia cultivar Peterstar, disclosed in U.S. Plant Pat. No. 8,259, in flower bract color. However, in side-by-side comparisons conducted in Encinitas, Calif., plants of the new Poinsettia differed from plants of the cultivar Peterstar in the following characteristics:

1. Plants of the new Poinsettia are more compact, shorter and less vigorous than plants of the cultivar Peterstar.
2. Plants of the new Poinsettia are not as freely branching as plants of the cultivar Peterstar.
3. Plants of the new Poinsettia have fewer and smaller leaves than plants of the cultivar Peterstar.
4. Leaves of the new Poinsettia are variegated whereas leaves of the cultivar Peterstar are solid green.

5. Plants of the new Poinsettia have smaller inflorescences than plants of the cultivar Peterstar.
6. Plants of the new Poinsettia have fewer cyathia per inflorescence than plants of the cultivar Peterstar.

BRIEF DESCRIPTION OF THE PHOTOGRAPHS

The accompanyng colored photograph illustrates the overall appearance of the new Poinsettia, showing the colors as true as it is reasonably possible to obtain in colored reproductions of this type. Colors in the photograph may differ slightly from the color values cited in the detailed botanical description which accurately describe the actual colors of the new Poinsettia. The photograph comprises a top perspective view of a typical plant of 'Eda Pan 1'.

DETAILED BOTANICAL DESCRIPTION

The new Poinsettia has not been observed under all possible environmental conditions. The phenotype may vary somewhat with variations in environment such as temperature, daylength and light intensity, without, however, any variance in genotype. The following observations and measurements describe plants grown in Encinitas, Calif., under commercial practice in a fiberglass-covered greenhouse with day temperatures about 19 to 31° C., night temperatures about 18 to 20° C., and light levels about 4,000 foot-candles. Plants were grown in 16.5-cm pots, pinched one time, and flowered under naturally lengthening nights during the fall.

In the following description, color references are made to The Royal Horticultural Society Colour Chart except where general terms of ordinary dictionary significance are used.

Botanical classification: *Euphorbia pulcherrima* Willd. cultivar Eda Pan 1.

Parentage: Naturally-occurring whole plant mutation of *Euphorbia pulcherrima* Willd. cultivar Supjisil, not patented.

Propagation:

*Type cutting.*—Terminal cuttings.

*Time to initiate roots.*—Summer: About 7 days at 24° C. Winter: About 10 days at 22° C.

*Time to develop roots.*—Summer: About 26 days at 24° C. Winter: About 26 days at 22° C.

*Rooting habit.*—Thick, freely branching.

Plant description:

*Plant form.*—Inverted triangle, top of plant rounded; mounding.

*Growth habit.*—Very compact, upright and somewhat spreading. Freely branching. Branching is enhanced by removing the shoot apex. Low to moderate vigor.

*Plant height.*—About 18 cm.

*Plant width.*—About 30 cm.

*Crop time.*—From unrooted cuttings to a flowering plant in a 16.5-cm container, about 18 weeks are required.

*Stem description.*—Number of lateral branches: About 6 lateral branches develop after removal of the terminal apex. Lateral branch length: About 12 cm. Internode length: About 7.5 mm. Stem color: 146A to 146B.

*Foliage description.*—Quantity of leaves per lateral branch: About 6. Length: About 9.5 cm. Width: About 6 cm. Shape: Ovate or tri-lobate. Apex: Acuminate. Base: Acute. Margin: Entire. Texture: Smooth; glabrous with very slight pubescence on lower surface. Color: Young foliage, upper surface: 146B; surrounded by 147C; margin, 2D. Young foliage, lower surface: 147B; margin, 2D. Mature foliage, upper surface: Center, 147B; surrounded by 148C; margin, 2D; occasionally tinge of anthocyanin on uppermost leaves. Mature foliage, lower surface: 147B to 147C; margin, 2D. Venation, upper surface: 47B. Venation, lower surface: 48D. Petiole: Length: About 4.5 cm. Diameter: About 2 mm. Color: 47A.

Inflorescence description:

*Inflorescence type and habit.*—Inflorescences are compound corymbs of cyathia with colored flower bracts subtending the cyathia.

*Natural flowering season.*—Autumn/winter in Northern Hemisphere. Flower initiation and development can be induced under long night conditions. Early flowering, response time is about 9.5 weeks.

*Quantity of inflorescences.*—One per lateral branch, usually about 6 per plant.

*Inflorescence size.*—Diameter: About 22 cm. Height (depth): About 3 cm.

*Flower bracts.*—Quantity of flower bracts per inflorescence: Usually about 9 primary bracts and about 7 smaller secondary bracts per inflorescence. Length, largest bracts: About 13 cm. Width, largest bracts: About 8 cm. Shape: Mostly ovate. Apex: Acuminate. Base: Acute. Margin: Entire. Texture: Smooth, velvelty. Aspect: Mostly flat, occasionally slightly rugose. Color: Upper surface: 45B. Lower surface: 45C; color does not fade.

*Cyathia.*—Quantity: Usually about 8 per corymb. Diameter of cyathia cluster: About 2 by 2.5 cm. Length: About 1 cm. Width: About 6 mm. Color: Immature: 144A to 144B. Mature: 144A.

*Peduncle.*—Length: About 4 mm. Aspect: Strong, erect. Color: 144B.

*Reproductive organs.*—Stamens: Stamen number: Typically about 3 per cyathium. Anther shape: Oblong. Anther length: About 1 mm. Anther color: 47A. Amount of pollen: Scarce. Pollen color: 8A. Pistils: Not observed. Nectary color: 10A.

Disease resistance: Resistance to pathogens common to Poinsettias has not been observed on plants grown under commercial conditions.

Post-production longevity: Generally plants maintain good substance and bract color for about four to six weeks under interior conditions.

It is claimed:

1. A new and distinct cultivar of Poinsettia plant named 'Eda Pan 1', as illustrated and described.

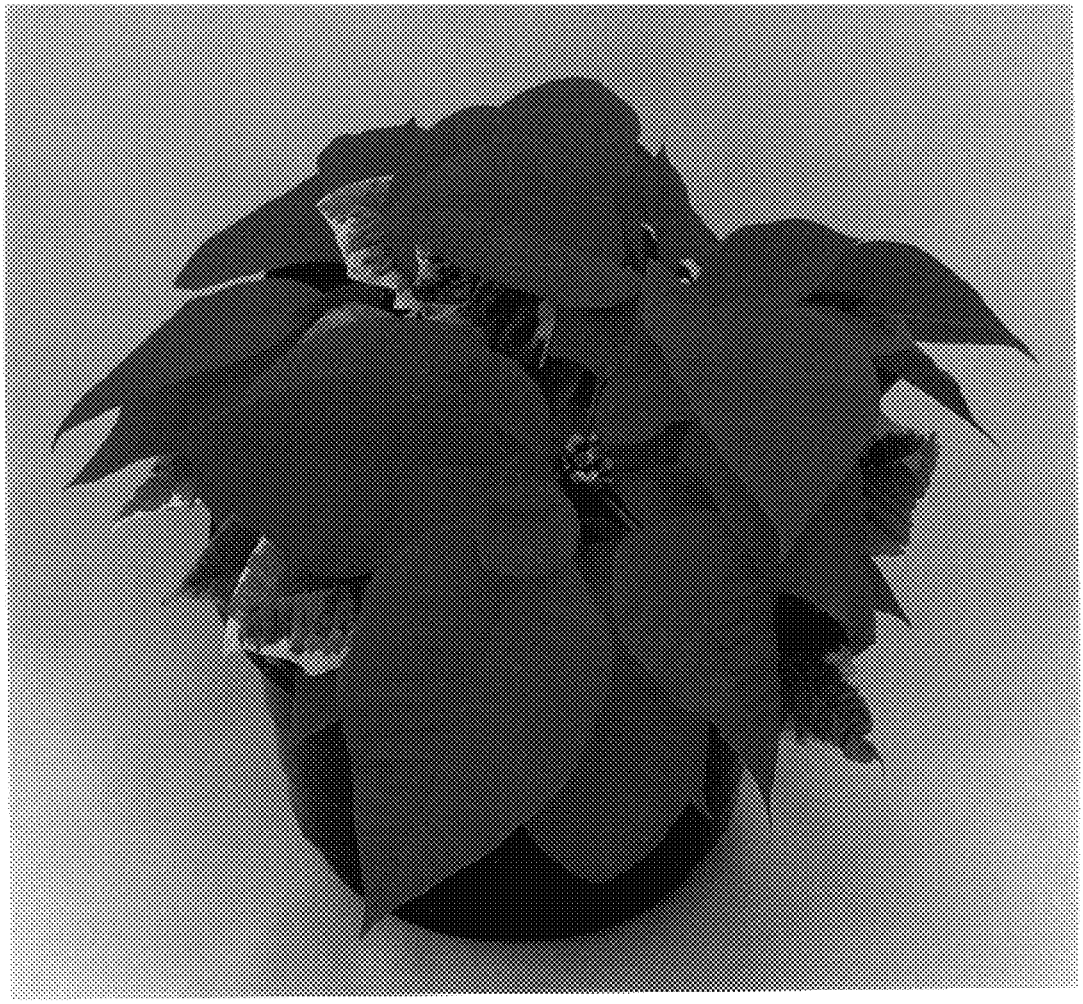

* * * * *